United States Patent [19]

Aumueller et al.

[11] Patent Number: 4,837,403
[45] Date of Patent: Jun. 6, 1989

[54] NOVEL POLYALKYLPIPERIDINE DERIVATIVES HAVING ALKYLENE BRIDGES, USE THEREOF AS STABILIZERS, AND INTERMEDIATES

[75] Inventors: Alexander Aumueller, Deidesheim; Peter Neuman, Wiesloch; Hubert Trauth, Dudenhofen, all of Fed. Rep. of Germany

[73] Assignee: BASF Aktiengesellschaft, Ludwigshafen, Fed. Rep. of Germany

[21] Appl. No.: 132,331

[22] Filed: Dec. 14, 1987

[30] Foreign Application Priority Data

Dec. 22, 1986 [DE] Fed. Rep. of Germany .... 3643890

[51] Int. Cl.$^4$ ............................................ C07D 251/00
[52] U.S. Cl. .................................. 544/215; 544/212; 544/216
[58] Field of Search .................. 544/212, 215, 216

[56] References Cited

U.S. PATENT DOCUMENTS 4,664,714 5/1987 Katsura et al. .................. 544/212

FOREIGN PATENT DOCUMENTS 2291203 11/1974 France ............................. 544/212

Primary Examiner—Mary C. Lee
Assistant Examiner—J. Richter
Attorney, Agent, or Firm—Oblon, Fisher, Spivak, McClelland & Maier

[57] ABSTRACT

Compounds useful as stabilizers have the general formula I $$C-A-B-A- \qquad (I)$$

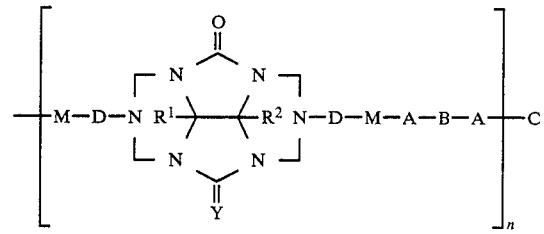

where the radicals are as defined in claim 1.

18 Claims, No Drawings

NOVEL POLYALKYLPIPERIDINE DERIVATIVES HAVING ALKYLENE BRIDGES, USE THEREOF AS STABILIZERS, AND INTERMEDIATES

It is known that 2,2,6,6-tetraalkylpiperidine derivatives are light stabilizers for organic polymers. Unsatisfactory aspects thereof are frequently the compatibility with polyolefins, the duration of the stabilizing action, the volatility and the self-color of the substances.

FR-A No. 2,291,203 describes glycoluril derivatives of the formula

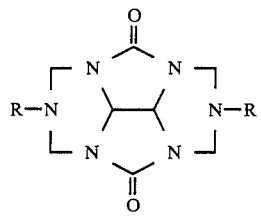

where R is optionally substituted hydrocarbyl of up to 22 carbon atoms. These compounds are proposed to be used as surfactants for the textile industry and as corrosion inhibitors.

It is an object of the present invention to provide new polyalkylpiperidine derivatives which avoid the above-mentioned disadvantages.

We have found that this object is achieved with polyalkylpiperidine derivatives of the general formula I

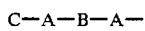

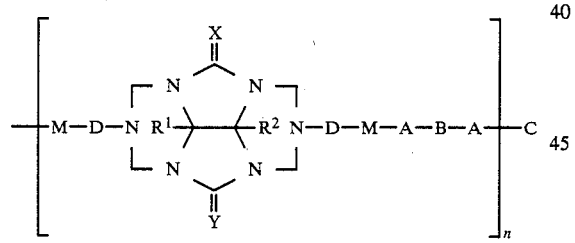

where
- n is an integer from 1 to 70,
- $R^1$ and $R^2$ are independently of each other hydrogen, $C_1$–$C_6$-alkyl, $C_7$–$C_{12}$-aralkyl, aryl or carboxylate or together a tetra-, penta- or hexamethylene group, or an optionally substituted radical of the formula

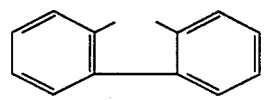

X and Y are independently of each other oxygen, sulfur, or $NR^7$, where $R^7$ is hydrogen, $C_1$–$C_8$-alkyl or $C_7$–$C_{12}$-aralkyl,
M is

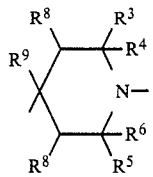

where $R^3$, $R^4$, $R^5$ and $R^6$ are identical or different and each is alkyl, or where $R^3$ and $R^4$ and also $R^5$ and $R^6$, together with the carbon atom to which they are bonded, form a 5- or 6-membered ring, and where $R^8$ is hydrogen or alkyl, or together with the associated carbon atom forms a

group and where $R^9$ is hydrogen or a further bond to a spiro-linked bridge member —B— (—A— is in this case a direct bond), the D's are identical or different and each is a (—CH$_2$—)$_m$ group, where m is a number from 1 to 20, or, if the radical M is bonded to —A— via the nitrogen atom, can also be a direct bond, one or more —M—D— groups being present in the molecule where the radical —M— is bonded to —D— via its nitrogen atom, the A's are identical or different and each is oxygen, optionally monosubstituted nitrogen, carboxyl, carbonyl, sulfonyl, sulfonamido or a direct bond, B is a bridge member or a direct bond, and C is hydrogen, acyl, chlorine, bromine, iodine, hydroxyl, amino, substituted amino, alkoxy, carboxyl, carboxylate, cyano, sulfonamido, optionally substituted carbonyl, an optionally substituted heterocycle, a urea group or a urethane group, or a group of the formula

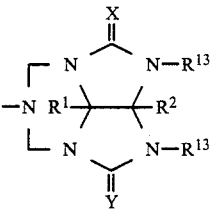

where the radicals $R^{13}$ are identical or different and each is hydrogen or $CH_2OR^{14}$, where $R^{14}$ is hydrogen or $C_1$–$C_{22}$-alkyl which may be interrupted by etheroxygen, nitrogen or sulfur, or where the radicals $R^{13}$ together can be a group

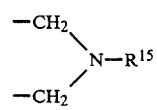

where $R^{15}$ has the meanings $C_1$–$C_{22}$-alkyl, which may be interrupted by etheroxygen, sulfur or nitrogen, $C_1$–$C_{22}$-alkenyl, $C_3$–$C_{12}$-cycloalkyl, optionally substituted $C_7$–$C_{12}$-aralkyl, $C_3$–$C_{12}$-alkynyl, nonaromatic heterocycle, $C_1$–$C_{22}$-alkyl or aralkyl, which in each case contain a heterocycle, or $C_1$–$C_{22}$-alkyl, which contains hydroxyl, thiol, cyano, carboxyl, carboxylate, optionally substituted carbamoyl, bromine, chlorine, iodine, sulfone, sulfone oxide, sulfonyl, optionally substituted sulfonamide, a urethane radical or urea radical, or where in the general formula (I) the group —M—A—B—A—C is a group of the general formula

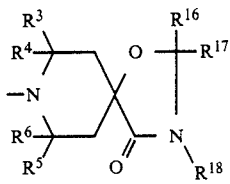

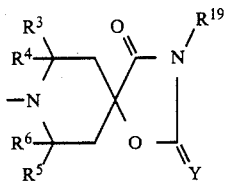

or

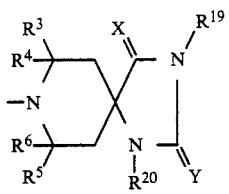

where $R^3$ to $R^6$ and also X and Y are as defined above, $R^{16}$ and $R^{17}$ are independently of each other hydrogen, optionally etheroxygen-, sulfur- or nitrogen-interrupted or cyano-, carboxyl-, carbonyl-, carbamoyl-, carboxylate- or keto-substituted $C_1$–$C_{22}$-alkyl, $C_3$–$C_{12}$-cycloalkyl, bicycloalkyl, tricycloalkyl, optionally chlorine-, $C_1$–$C_{22}$-alkyl- or $C_1$–$C_{22}$-alkoxy-substituted aryl, or $C_7$–$C_{22}$-aralkyl or where $R^{16}$ and $R^{17}$ together with the carbon atom joining them form a $C_5$–$C_{18}$-cycloalkyl group which may be substituted by up to 4 $C_1$–$C_4$-alkyl groups, or a group of the formula

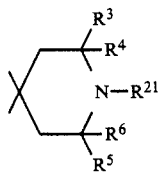

where $R^{21}$ is hydrogen, $C_1$–$C_{22}$-alkyl, which may be interrupted by etheroxygen, sulfur or nitrogen or substituted by cyano, hydroxyl, thiol, carboxyl, carbamoyl or carboxylate, $C_1$–$C_{22}$-alkenyl or $C_1$–$C_{22}$-C-acyl, and $R^3$, $R^4$, $R^5$ and $R^6$ have the above-mentioned meanings, $R^{18}$ is hydrogen, $C_1$–$C_{22}$-alkyl, which may be substituted by etheroxygen, sulfur or nitrogen or substituted by cyano, carboxyl, carbamoyl, carboxylate, hydroxyl, thiol or amino, or $C_1$–$C_{22}$-C-acyl, $R^{19}$ is hydrogen, $C_1$–$C_{22}$-alkyl, which may be interrupted by etheroxygen, sulfur or nitrogen or substituted by cyano or carboxylate, aryl, which can be optionally substituted by chlorine, $C_1$–$C_{22}$-alkyl or $C_1$–$C_{22}$-alkoxy, $C_7$–$C_{22}$-aralkyl or $C_3$–$C_{12}$-cycloalkyl and $R^{20}$ is hydrogen or optionally branched alkyl, and the acid addition salts and hydrates of these compounds.

The present invention also relates to mixtures of compounds according to the invention of the general formula I.

The present invention further relates to intermediates for preparing the compounds of the general formula I. The intermediates conform to the general formulae II, III, IV and V:

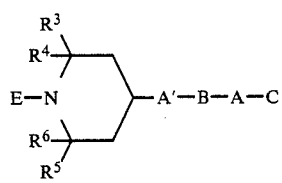

(II)

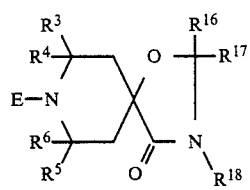

(III)

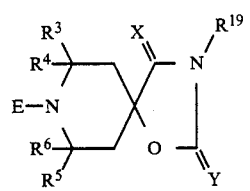

(IV)

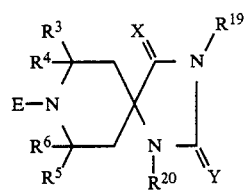

(V)

where

E is NC—$CH_2$— or $H_2N$—$CH_2$—$CH_2$—,

—A'— is optionally monosubstituted nitrogen, carboxyl, carbonyl, sulfonyl, sulfonamido or a direct bond, and —A—, —B—, —C, X, Y, $R^3$, $R^4$, $R^5$, $R^6$, $R^{16}$, $R^{17}$, $R^{18}$, $R^{19}$ and $R^{20}$ have the abovementioned meanings, and the acid addition salts and hydrates thereof.

Preference is given to compounds where n is from 1 to 20, in particular where n is 1.

Specific examples of $R^1$ and $R^2$, besides hydrogen, are methyl, ethyl, propyl, butyl, pentyl, hexyl, benzyl, phenylethyl, phenylpropyl, phenylbutyl, methylbenzyl, phenyl, tolyl, carbomethoxy, carboethoxy, carbopropoxy and carbobutoxy.

Preferred $R^1$ and $R^2$ are methyl, ethyl, benzyl, phenyl and in particular hydrogen, methyl and phenyl.

The term "alkyl" signifies straight-chain or branched alkyl, in particular $C_1$-$C_{22}$-alkyl, preferably $C_1$-$C_6$-alkyl, particularly preferably $C_1$-$C_4$-alkyl. Examples of $C_1$-$C_4$-alkyls $R^3$ to $R^6$ are thus methyl, ethyl, propyl and butyl. In the case of the radicals $R^3$ to $R^6$, two adjacent radicals can also form a tetra-, penta- or hexamethylene group.

Preferably, $R^3$ to $R^6$ are methyl.

X and Y are independently of each other in particular oxygen, but also sulfur or $NR^7$, where $R^7$ has the above-mentioned meanings.

A can have, for example, the following meanings:

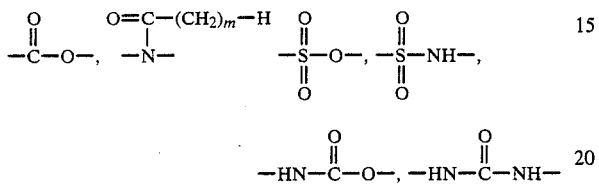

or a direct bond, where m is 0-20. A is particularly preferably oxygen.

Bridge members B are divalent aliphatic, araliphatic or aromatic groups which can also contain hetero atoms, namely oxygen, nitrogen or sulfur, and also in particular a direct bond.

There may be mentioned in particular alkylene, cycloalkylene, aralkylene, CO- or $SO_2$-interrupted or -substituted alkylene, aralkylene or arylene.

Specific bridge members B are for example:

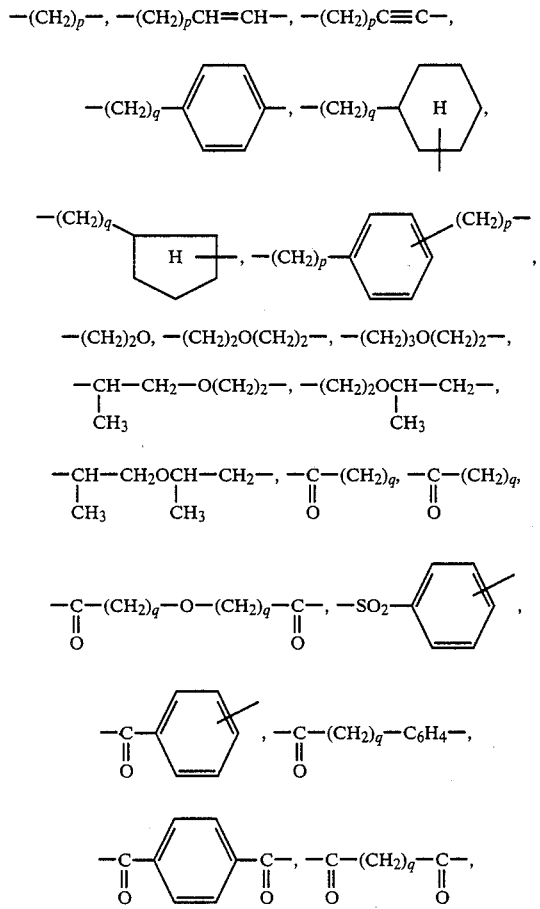

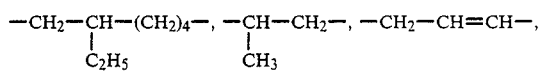
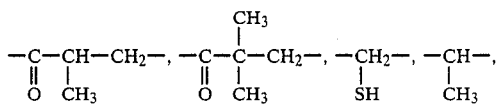
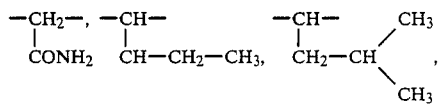
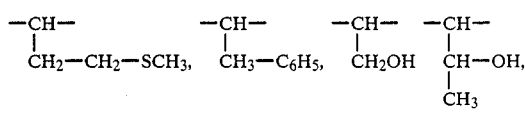
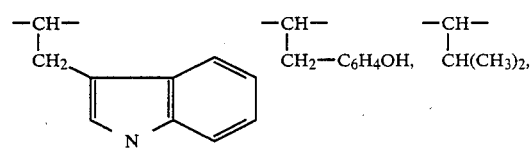
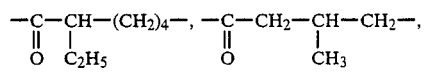
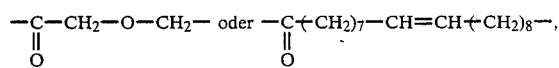

where p is 1-20 and q is 0-20.

The bridge members can also be bonded to the radical —M— by way of a spirolinkage. The bridge member —B— then for example has the following structure:

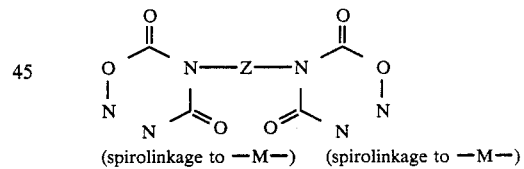

where Z is a bridge member, for example —$(CH_2)_k$— (k=0-20), phenylene,

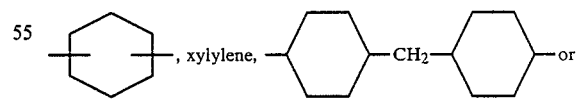

(E=O, N, S, $SO_2$, SO, —$CH_2$—, —$CH_2$—$CH_2$—, direct bond).

Further examples of bridge members —B— are the following:

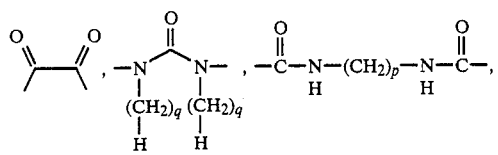
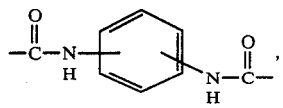
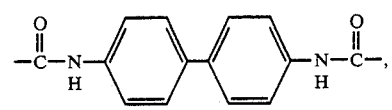
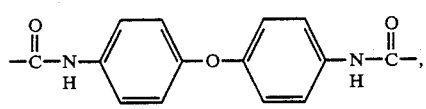
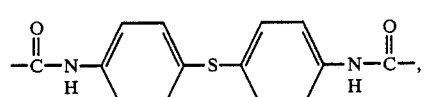
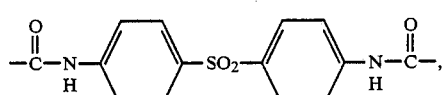
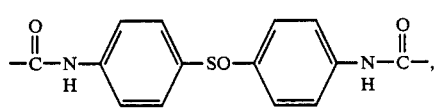
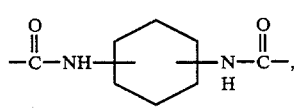
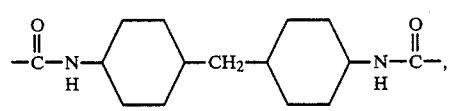
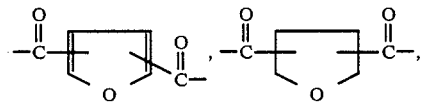
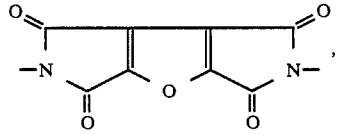
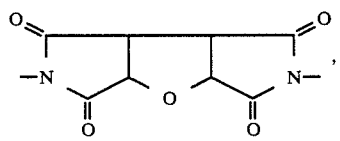
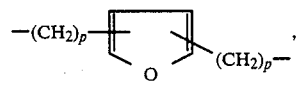
-continued
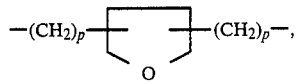
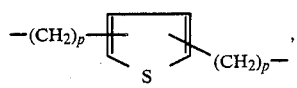
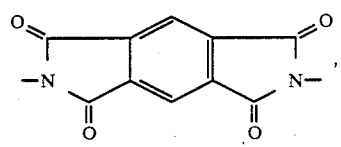
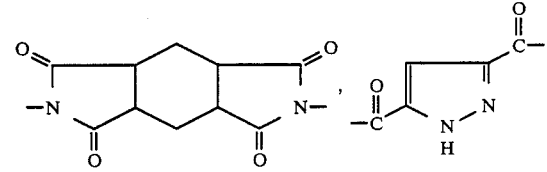
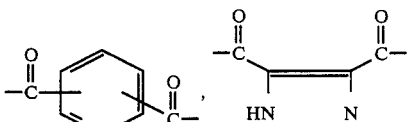
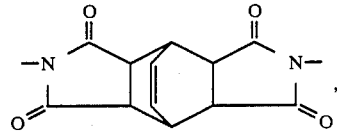
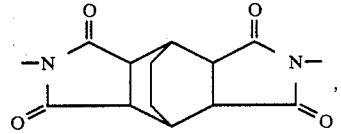
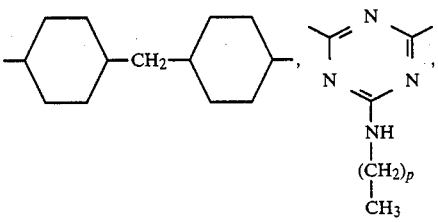
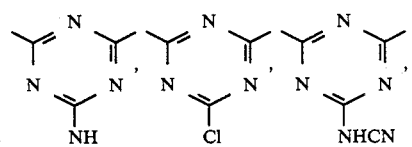

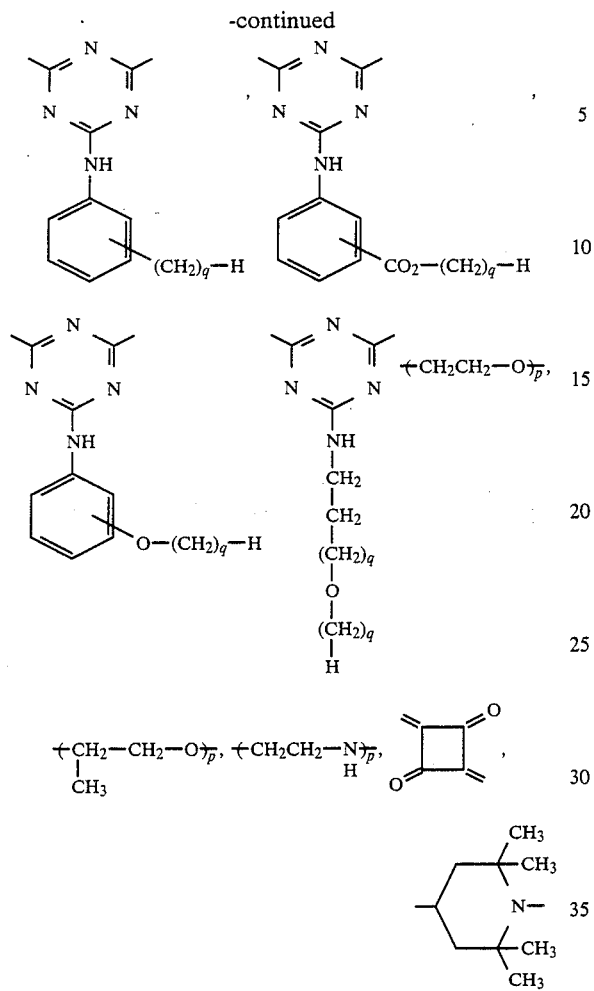
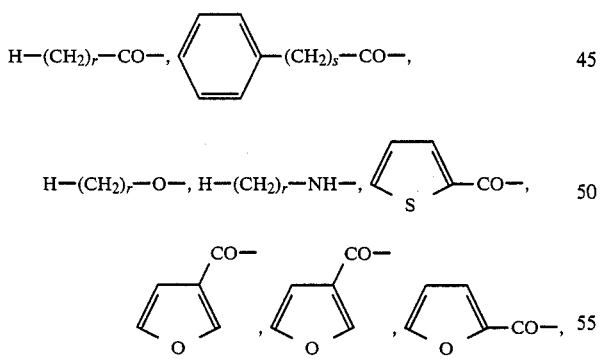
where p is 1-20 and q is 0-20.
Examples of end groups C are:
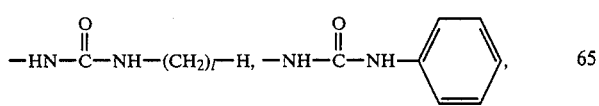
where r is 0-20 and s is 1-5.
Preferably, C is $CH_3CO$, $CH_3CH_2CO$ or in particular hydrogen.
Urea groups are for example:
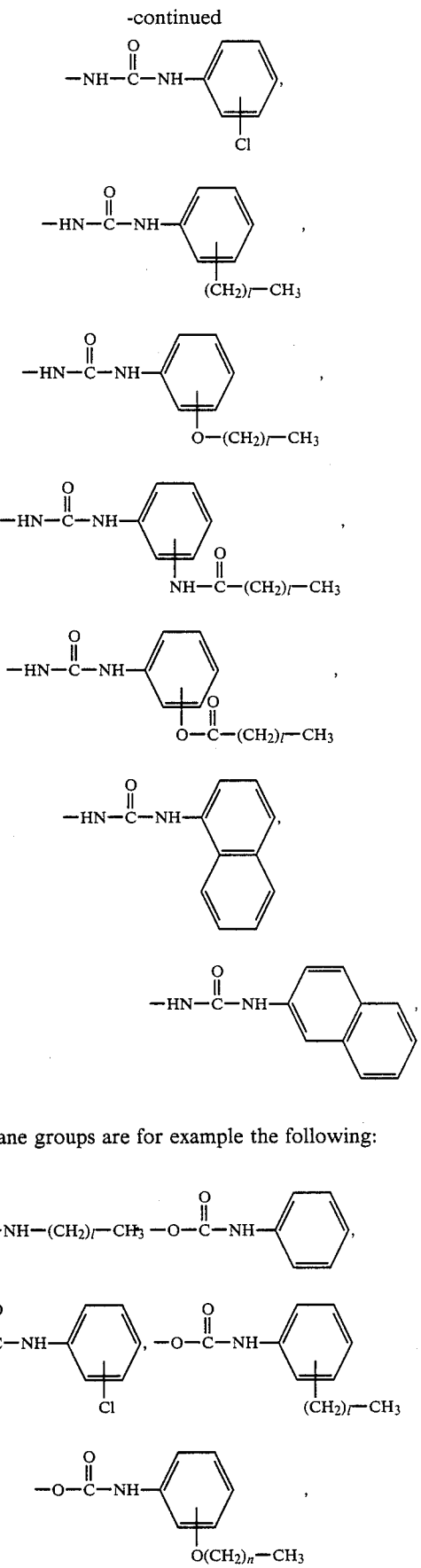
l = 0-22
Urethane groups are for example the following:

-continued
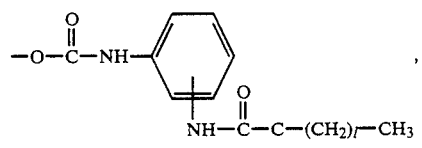
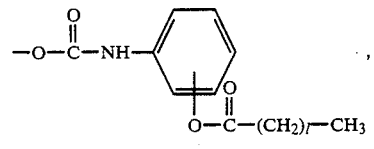
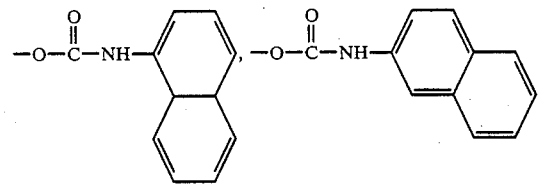
(l = 0–22)
Further examples of end groups C are the following:
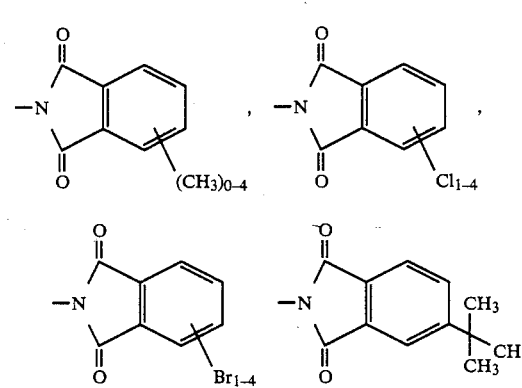
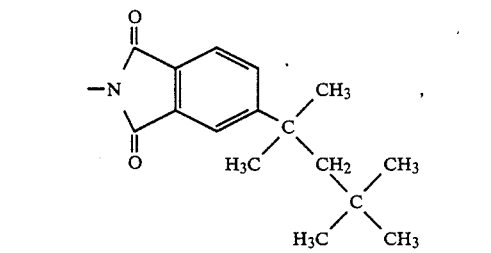
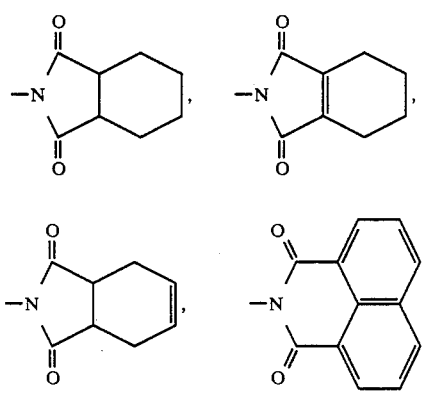
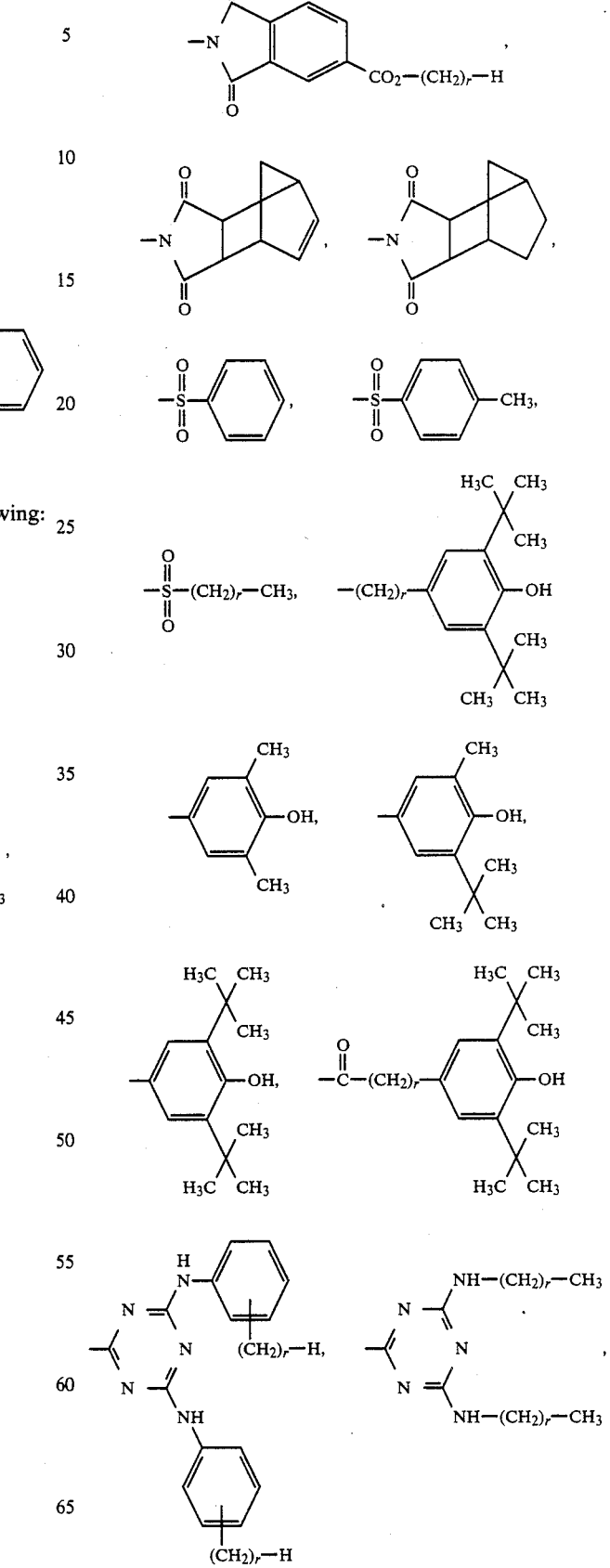

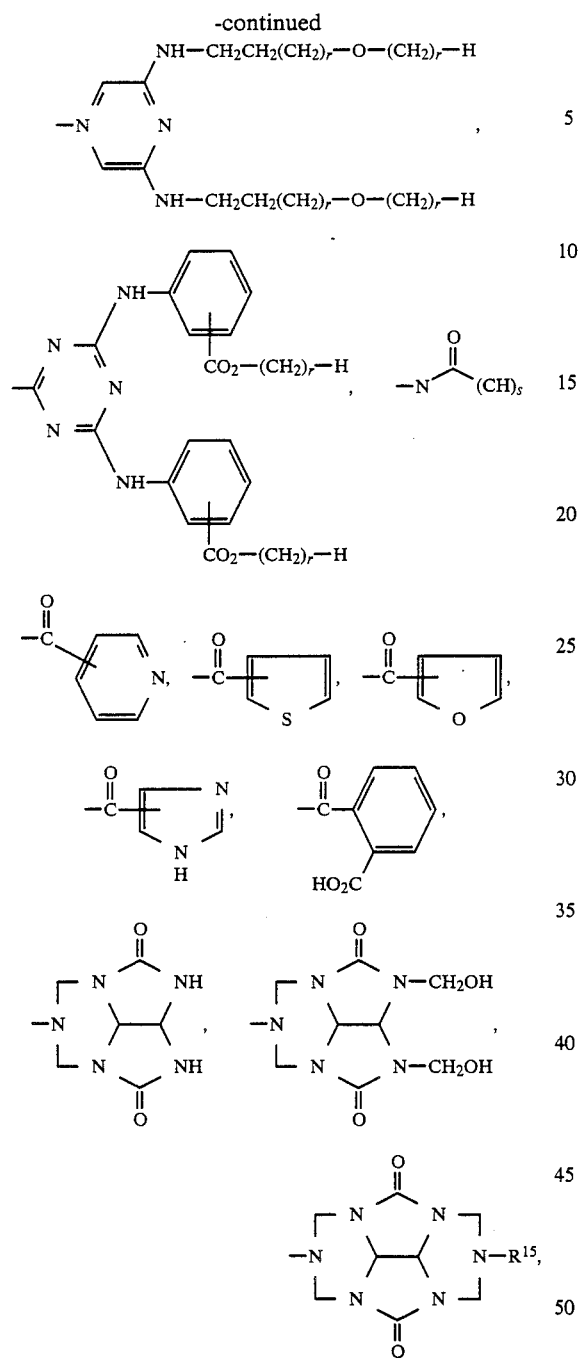
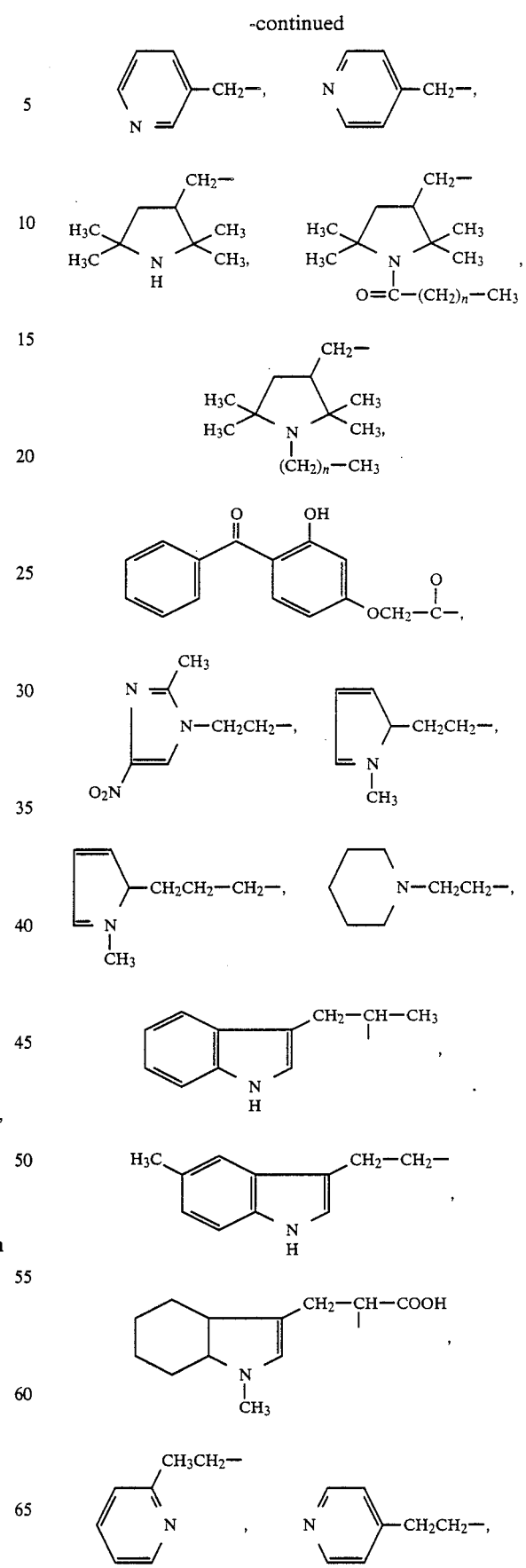
where R[15] has the meanings specified in claim 1 and in the description.
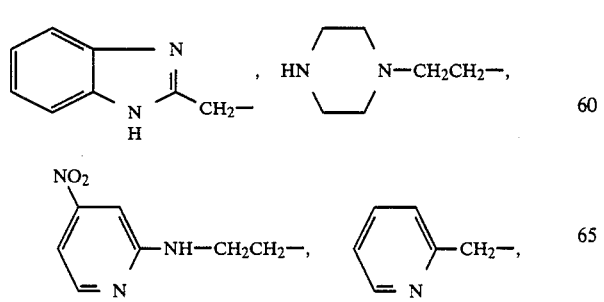

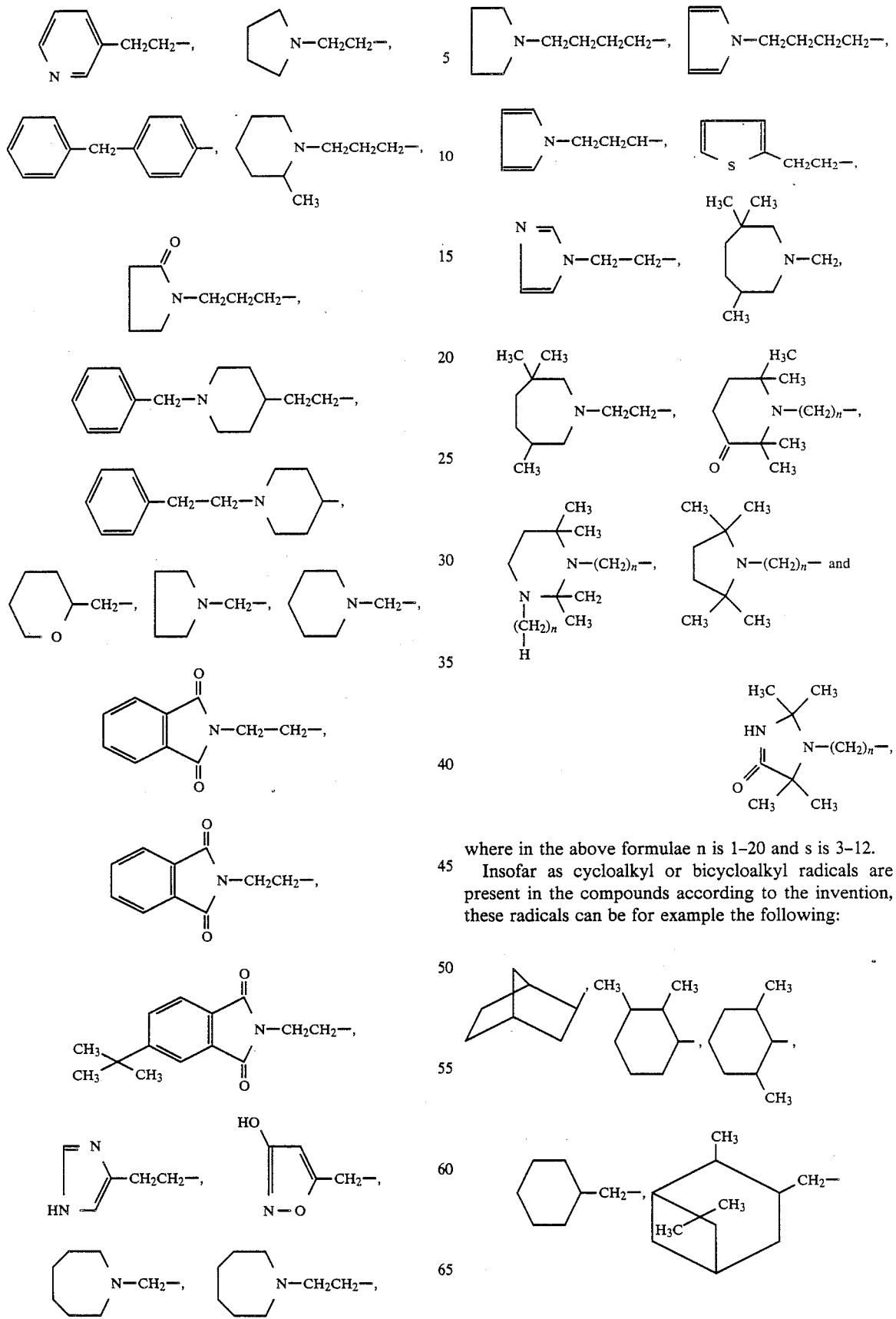
where in the above formulae n is 1–20 and s is 3–12.
Insofar as cycloalkyl or bicycloalkyl radicals are present in the compounds according to the invention, these radicals can be for example the following:

-continued
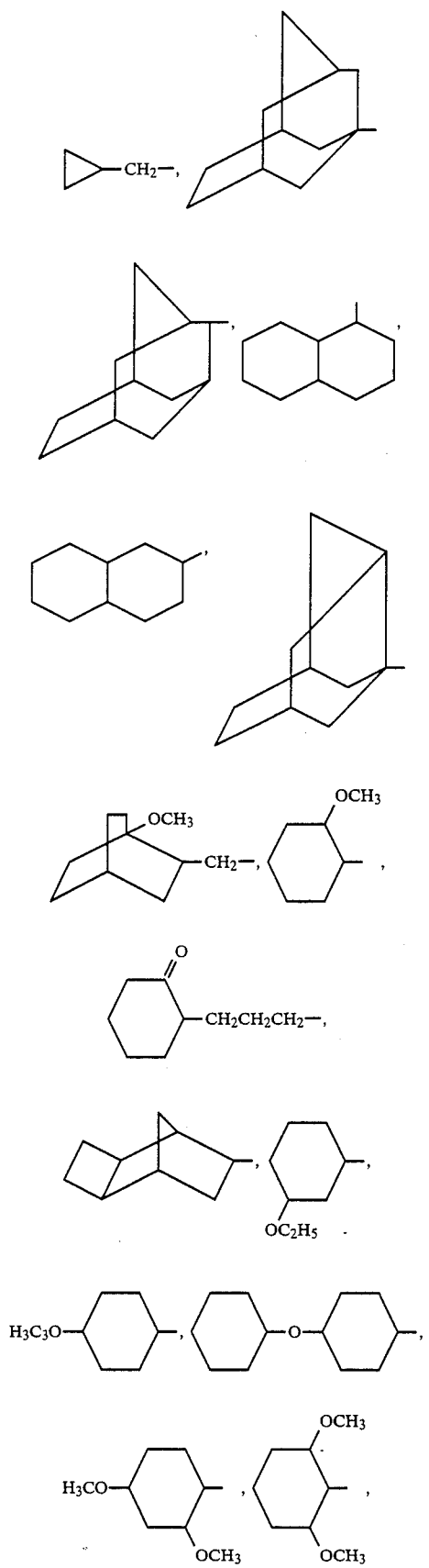
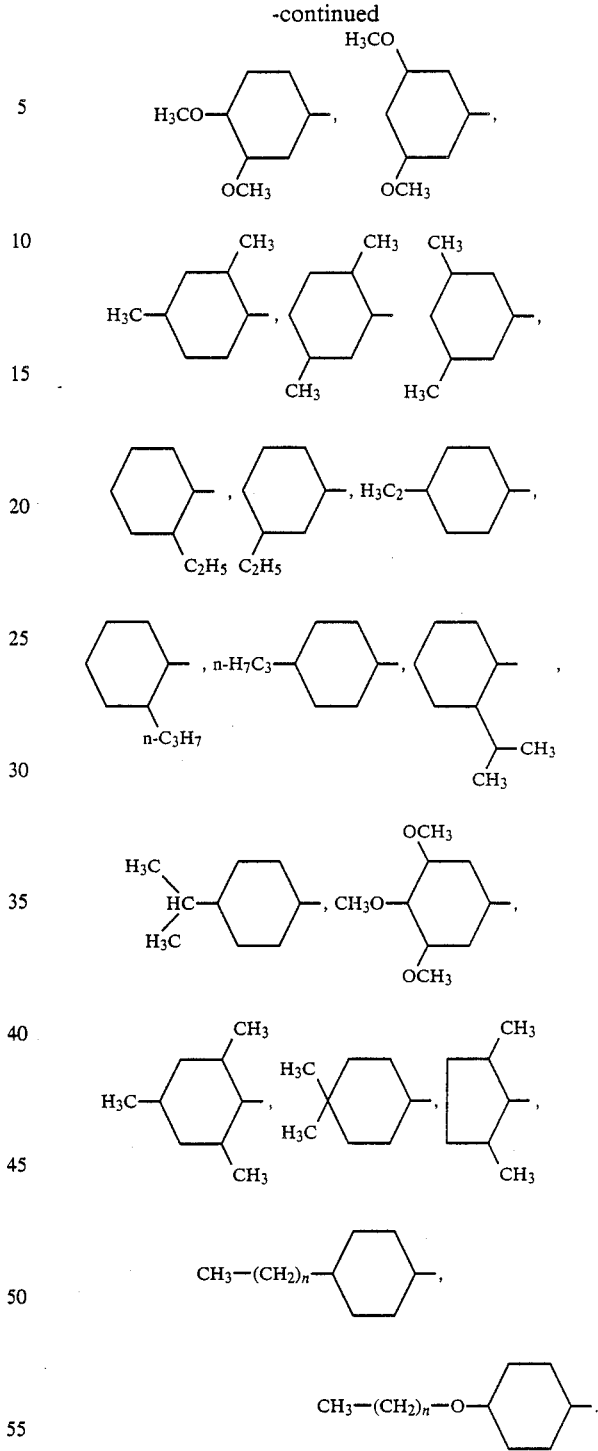
Insofar as hydroxyl-substituted or carboxyl-substituted alkyl radicals are present in the compounds according to the invention, these radicals can be for example the following:
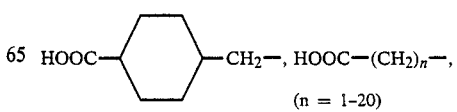
(n = 1-20)

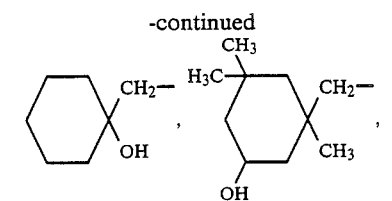 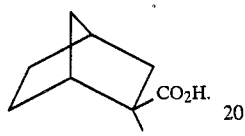
HO—CH₂CH₂O—CH₂CH₂—, HO—(CH₂)ₙ—,
(n = 1-20)
H—(CH₂)ₙ—C(=O)—NH—(CH₂)ₘ—, and
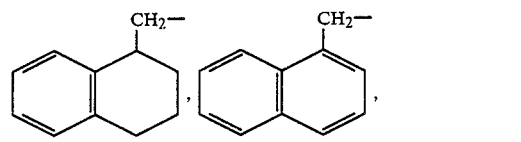
Insofar as aralkyl radicals are present in the compounds according to the invention, these radicals can be for example the following:
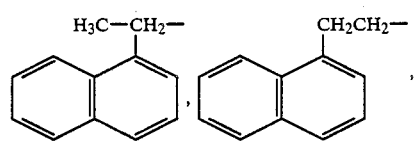
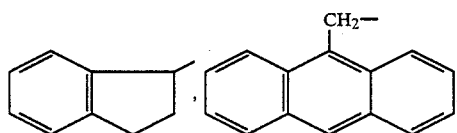
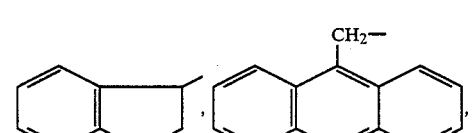
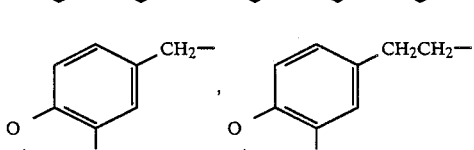
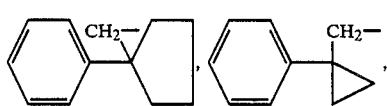
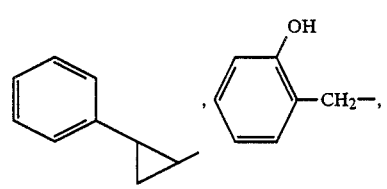
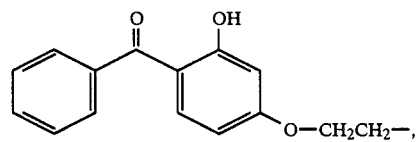
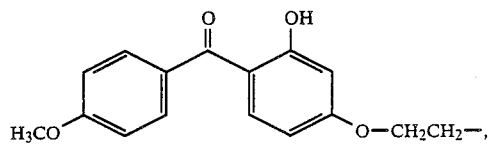
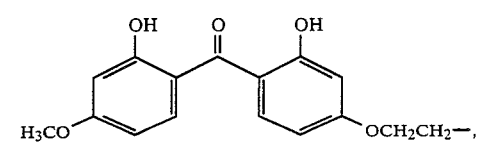
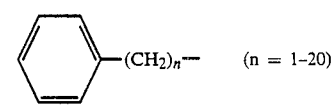 (n = 1-20)
Insofar as nonaromatic heterocycles are present in the compounds according to the invention, these heterocycles can be for example the following
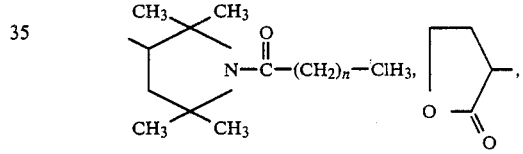
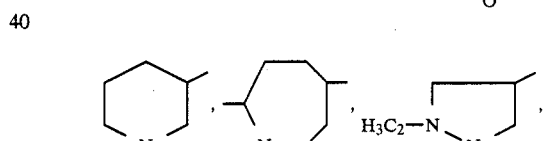
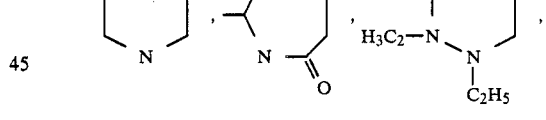
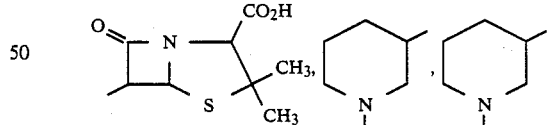
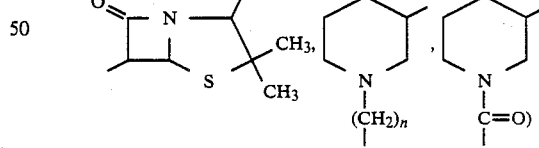
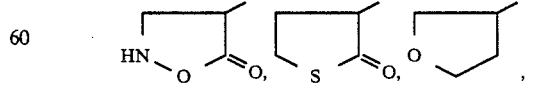
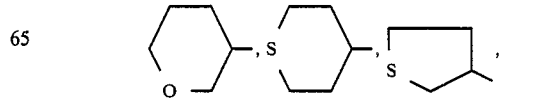

-continued

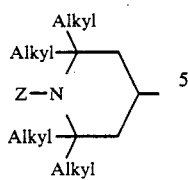

(Z=hydrogen, alkyl, acyl, HO—).

The term "optionally substituted" used in connection with the definitions of radicals encompasses the possible meanings explained above. It encompasses in particular substituents such as $C_1$-$C_6$-alkyl, $C_1$-$C_6$-alkoxy, $C_2$-$C_{12}$-carboxylate, $C_1$-$C_{12}$-C-acyl, halogen, nitro, carboxyl, amino, hydroxyl, —SH, —S—$C_1$-$C_4$-alkyl, phenyl, $C_2$-$C_6$-alkenyl, (poly)ethoxy and (poly)amino.

The term "-C-acyl", signifies for example $C_{14}$-$C_{20}$-C-acyl, in particular radicals of the formula

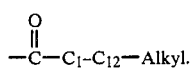

Compounds of the general formula (I) where n=1 can be prepared by reaction of compounds of the general formula (I') with compounds of the general formula (II) by the process of FR-A No. 2,291,203.

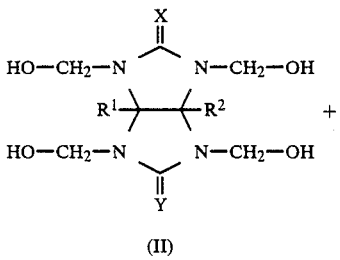

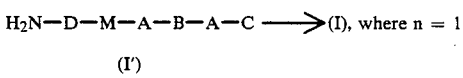

Compounds of the general formula I where n is 1 can be prepared by reaction of compounds of the general formula (I') where D is not a direct bond and compounds of the general formula (I') where D is a direct bond. In this reaction, the compounds of the general formula (I') can be added simultaneously or in any desired order to compounds of the general formula (I). In this case, the reaction generally gives rise to mixtures of the expected products, which, if desired, can be separated into the individual products in a conventional manner.

The compounds of the general formula (I') can also be prepared in situ by reacting compounds of the general formula (I''') with formaldehyde or a source thereof.

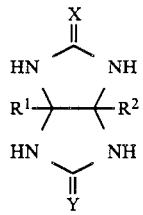

Compounds of the general formula (I) with free amino or hydroxyl groups can be converted by literature methods into the corresponding acylated and alkylated products.

If the acylating or alkylating agent used is a compound having more than one reactive group, the product is a compound of the general formula (I) where n is greater than 1.

The same is true of reactions with isocyanates to give the corresponding urethanes and ureas. Compounds of the general formula (I) having free carboxyl groups or carboxylate groups from lower alcohols can be converted by esterification, aminolysis or transesterification into the corresponding esters and amides. If the alcohol, amine or aminoalcohol used in the reaction is a compound having more than one reactive group, the product obtained is a compound of the general formula (I) where n is greater than 1.

Compounds of the general formula (I) where n is greater than 1 can also be prepared by reacting compounds of the general formula (II) with compounds of the general formula (I'').

$$H_2N-D-M-A-B-A-M-D-NH_2 \qquad (I'')$$

By subsequent addition of an amine $R^{15}$-$NH_2$, the product can be end group capped. Here too, the compounds of the general formula (II) can be produced in situ by reacting compounds of the general formula (I''') with formaldehyde or a source thereof.

The compounds according to the invention can be present in the form of the free bases or as salts. Suitable anions come for example from inorganic acids and in particular organic carboxylic acids and also organic sulfonic acids.

The compounds according to the invention have extremely good stabilizing properties, and no self-color, are highly compatible with organic polymers, and have a low vapor pressure.

Inorganic anions are for example chloride, bromide, sulfate, isosulfate, tetrafluoroborate, phosphate and thiocyanate.

Carboxylic acid anions are for example formate, acetate, propionate, hexanoate, cyclohexanoate, lactate, stearate, dodecylbenzoate, benzoate, acrylate, methacrylate, citrate, malonate, succinate and anions of polycarboxylic acids having up to 3,000 COOH groups.

Sulfonic acid anions are for example benzenesulfonate and tosylate.

The compounds according to the invention are suitable for stabilizing organic materials, especially plastics, to degradation by light and heat and are also effective as metal deactivators. They are added to the plastics to be stabilized in a concentration of from 0.01 to 5% by weight, preferably from 0.002 to 1% by weight, before, during or after polymer formation.

The compounds according to the invention can be mixed with the plastics to be stabilized by any known apparatus and method for mixing stabilizers or other additives in the polymers.

The plastics stabilized by one of the compounds according to the invention may also contain further additives, for example antioxidants, light stabilizers, metal deactivators, antistats, flame retardents, pigments and fillers.

Examples of antioxidants and light stabilizers which can be added to the plastics besides the compounds according to the invention are compounds based on sterically hindered phenols or sulfur- or phosphorus-containing costabilizers.

Specific examples of such phenolic antioxidants are 2,6-di-tert.-butyl-4-methylphenol, n-octadecyl-β-(3,5-di-tert.-butyl-4-hydroxyphenyl)propionate, 1,1,3-tris(2-methyl-4-hydroxy-5-tert.-butylphenyl)butane, 1,3,5-trimethyl-2,4,6-tris(3,5-di-tert.-butyl-4-hydroxybenzyl)-benzene, 1,3,5-tris(3,5-di-tert.-butyl-4-hydroxybenzyl-)isocyanurate, 1,3,5-tris[β-(3,5-di-tert.-butyl-4-hydroxyphenyl)propionyloxyethyl]isocyanurate, 1,3,5-tris(2,6-dimethyl-3-hydroxy-4-tert.-butylbenzyl)isocyanurate, pentaerythritol tetrakis[β-(3,5-di-tert.-butyl-4-hydroxyphenyl)propionate].

Examples of phosphorus-containing antioxidants are tris(nonylphenyl)phosphite, distearyl pentaerythritol diphosphite, tris(2,4-di-tert.-butylphenyl)phosphite, tris(2-tert.-butyl-4-methylphenyl)phosphite, bis(2,4-di-tert.-butylphenyl)pentaerythritol diphosphite and tetrakis(2,4-di-tert.-butylphenyl)-4,4'-biphenylene diphosphite.

Examples of sulfur-containing antioxidants are dilauryl thiodipropionate, dimyristyl thiodipropionate, distearyl thiodipropionate, pentaerythritol tetrakis(β-laurylthiopropionate) and pentaerythritol tetrakis(β-hexylthiopropionate).

Further antioxidants and light stabilizers which may be used together with the compounds according to the invention are for example 2-(2'-hydroxyphenyl)benzotriazoles, 2-hydroxybenzophenones, aryl esters of hydroxybenzoic acid, α-cyanocinnamic acid derivatives, nickel compounds and oxalic dianilides.

Examples of organic polymers which can be stabilized by the compounds according to the invention are:

polymers of mono- and diolefins, eg. low or high density polyethylene, linear low density polyethylene, polypropylene, polyisobutylene, polybutene-1, polyisoprene, polybutadiene and also copolymers of mono- or diolefins or mixtures thereof;

copolymers of mono- or diolefins with other vinyl monomers, eg. ethylene/alkyl acrylate copolymers, ethylene/alkyl methacrylate copolymers, ethylene/vinyl acetate copolymers or ethylene/acrylic acid copolymers;

polystyrene;

copolymers of styrene or α-methylstyrene with dienes or acrylic derivatives, eg. styrene/butadiene, styrene/acrylonitrile, styrene/ethyl methacrylate, styrene/butadiene/ethyl acrylate, styrene/acrylonitrile/methacrylate;

ABS, MBS or similar polymers;

halogen-containing polymers, eg. polyvinyl chloride, polyvinyl fluoride, polyvinylidene fluoride and copolymers thereof;

polymers derived from α,β-unsaturated acids and derivatives thereof, such as polyacrylates, polymethacrylates, polyacrylamides and polyacrylonitriles;

polymers derived from unsaturated alcohols and amines or their acrylic derivatives or acetals, such as polyvinyl alcohol and polyvinyl acetate;

polyurethanes, polyamides, polyureas, polyesters, polycarbonates, polysulfones, polyether sulfones and polyether ketones.

Further organic polymers which can be stabilized with the compounds according to the invention are industrial coatings. Of these, baking finish coatings, in particular automotive coatings, preferably of the two-build variety, are particularly noteworthy.

Here too the abovementioned antioxidants and light stabilizers may be used in addition.

The compounds according to the invention can be added to the coating solution in a solid or dissolved form. In this connection, their excellent solubility in coating systems is of particular advantage.

Preference is given to using the compounds according to the invention in polyolefins, preferably ethylene and propylene polymers.

Preference is further given to using the compounds according to the invention in polyurethanes. In said use they are preferably used combined with a UV absorber and/or an antioxidant.

The invention is illustrated in detail by the Examples below.

EXAMPLE 1

34 g (0.17 mol) of N-β-aminoethyl-4-hydroxy-2,2-6,6-tetramethylpiperidine and 44.5 g (0.085 mol) of a 50% strength aqueous solution of tetramethylolacetylenediurea are heated in 75 ml of water at 80° C. for 5.5 h. This is followed by filtering off with suction, drying and recrystallizing from acetonitrile. The compound crystallizes with 1 mol of water. 23.9 g (46% of theory) are obtained of colorless crystals having a melting point of 263° C. (dec.).

Calc.: C 59.2 H 9.3 N 18.4 O 13.1. Found: C 56.7 H 9.4 N 18.1 O 13.0.

The composition can be freed from water by boiling in toluene under a water separator.

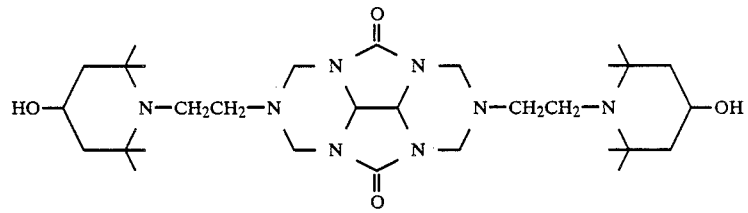

EXAMPLE 2

10.0 g (16.9 mmol) of the compound of Example 1 are dissolved in 150 ml of dichloromethane, and this solution is cooled down to 0°–10° C. At this temperature 3.5 g (45.0 mmol) of acetyl chloride are added dropwise.

After standing overnight the mixture is neutralized to pH 10 with sodium hydroxide solution, and the organic phase is concentrated. Recrystallization from methylcyclohexane gives 10.0 g (88%) of the diacetyl compound in the form of colorless crystals having a melting point of 236°–238° C.

Calc.: C 60.5 H 8.7 N 16.6 O 14.2. Found: C 60.4 H 8.9 N 16.2 O 14.5.

(b) 25 g of the product of (a) are hydrogenated in 300 ml of toluene together with 20 g of ammonia and 5 g of Raney nickel at 250 bar. This is followed by filtering, concentrating, and recrystallization of the residue from acetonitrile to give 19 g of N-[1-β-aminoethyl-2,2,6,6-tetramethyl-4-piperidinyl]myristamide having a melting point of 88°–89° C.

(c) 9.5 g of the product of (b) and 6.0 g of a 50%

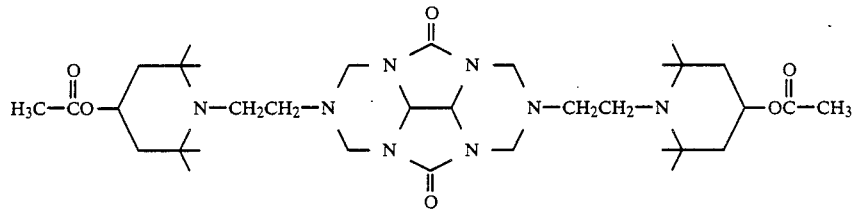

EXAMPLE 3

10.0 g of the compound of Example 1 are reacted with 5.9 g of propionic anhydride by the method of Example 2. Neutralization is followed by extraction with n-butanol, concentration of the butanol phase and recrystallization of the residue from methylcyclohexane to give 3.5 g (30%) of the dipropionyl compound in the form of colorless crystals having a melting point of 239° C.

Calc.: C 61.5 H 8.9 N 16.0 O 13.7. Found: C 61.6 H 9.1 N 16.2 O 13.7.

strength aqueous solution of tetramethylolacetylenediurea are boiled in 70 ml of isobutanol under a water separator for 5 h. The mixture is concentrated and the residue is recrystallized from acetonitrile to give 6.6 g of a compound of the formula

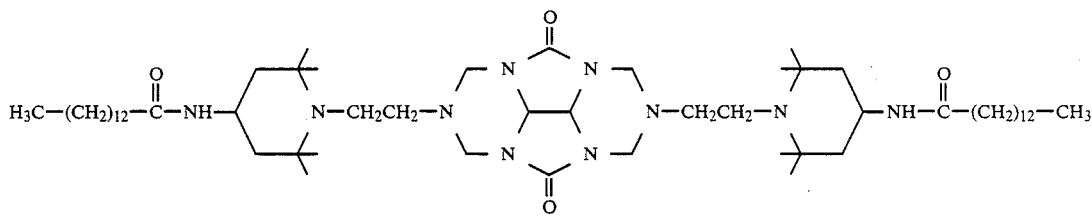

having a melting point of 135°–136° C.

Calc.: C 69.0 H 10.8 N 13.9 O 6.3. Found: C 69.0 H 10.9 N 13.0 O 6.8.

EXAMPLE 5

(a) 96 g of N-[2,2,6,6-tetramethyl-4-piperidinyl]-pentadecanoamide are reacted as in Example 4a. Recrystal-

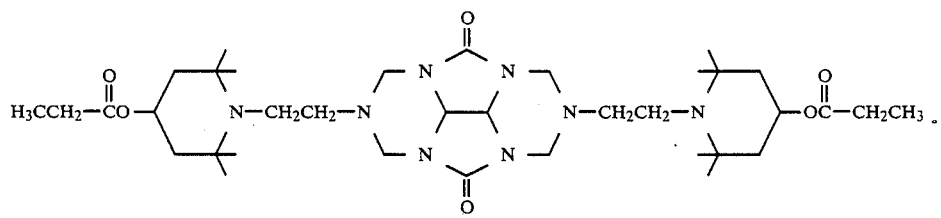

EXAMPLE 4

(a) 84 g (=0.23 mol) of N-[2,2,6,6-tetramethyl-4-piperidinyl]myristamide are dissolved in 150 ml of ethanol. 28 g of a 70% strength aqueous solution of glycollonitrile are added dropwise, and the mixture is heated at 70° C. for 40 h. The resulting precipitate is filtered off with suction, washed with ethanol and recrystallized twice from ethanol.

33 g are obtained of N-[1-cyanomethyl-2,2,6,6-tetramethyl-4-piperidinyl]myristamide having a melting point of 106° C.

Calc.: C 74.0 H 11.7 N 10.4 O 0.39. Found: C 74.2 H 11.7 N 10.4 O 4.0.

lization of the crude product from ethanol gives 62 g of N-[1-cyanomethyl-2,2,6,6-tetramethyl-4-piperidinyl]-pentadecanoamide having a melting point of 101° C.

Calc.: C 74.5 H 11.7 N 10.0 O 3.8. Found: C 74.5 H 11.8 N 9.9 O 3.9.

(b) 40 g of the product of (a) are hydrogenated as specified in Example 4b. The crude product is recrystallized from acetonitrile to give 35.8 g of N-[1-βaminoethyl-2,2,6,6-tetramethyl-4-piperidinyl]-pentadecanoamide having a melting point of 65° C.

(c) 35 g of the product of (b) are made to react with tetramethylolacetylenediurea by the method of Example 4c. Recrystallization from acetonitrile gives 28 g of a compound of the formula

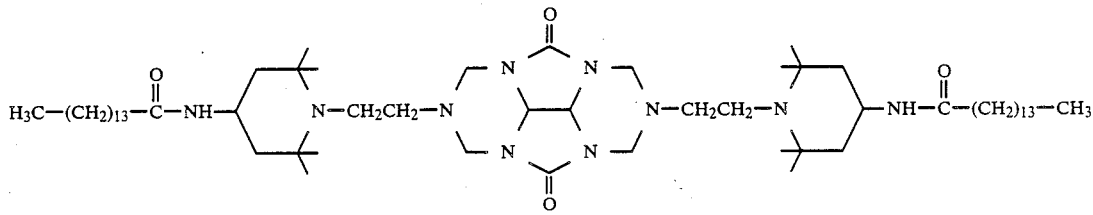

having a melting point of 157°–158° C.

Calc.: C 69.4 H 10.9 N 13.5 O 6.2. Found: C 69.0 H 10.9 N 13.1 O 6.4.

EXAMPLE 6

(a) 15 ml of ethanol saturated with potassium carbonate, 18 g of paraformaldehyde, 1.43 g of potassium carbonate and 51 g of acetonecyanohydrin were stirred at 25° C. for 2 h and then brought to pH 6 with 85% strength phosphoric acid. 75 ml of ethanol and 88 g of N-[2,2,6,6-tetramethyl-4-piperidinyl]pelargonamide were added, and the mixture was refluxed for 6.5 h. The reaction mixture was filtered, the filtrate was concentrated and the residue was recrystallized from n-heptane to give 82 g of N-[1-cyanomethyl-2,2,6,6-tetramethyl-4-piperidinyl]pelargonamide having a melting point of 68° C.

Calc.: C 71.6 H 11.0 N 12.5 O 4.8. Found: C 70.9 H 10.9 N 12.5 O 5.4.

(b) 40 g of the product of (a) were hydrogenated as in Example 4b. The mixture was filtered and the filtrate was concentrated. The oily residue of N-[1-β-aminoethyl-2,2,6,6-tetramethyl-4-piperidinyl]pelargonamide was further reactable without purification.

(c) 40 g of the product of (b) were made to react with tetramethylolacetylenediurea as in Example 4c. Concentrating and recrystallization from acetonitrile gave 26.3 g of a compound of the formula

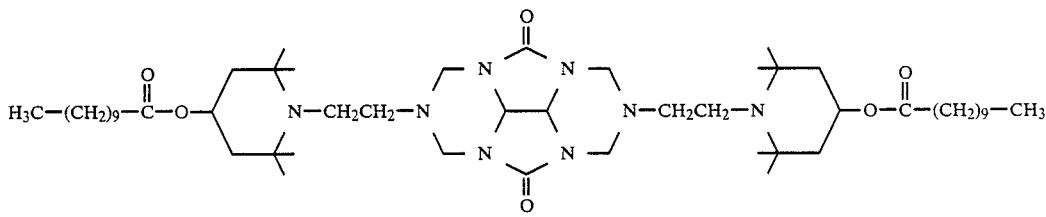

having a melting point of 138°–139° C.

EXAMPLE 7

(a) 87 g of 2,2,6,6-tetramethyl-4-piperidinyl undecanoate were reacted analogously to Example 6a. Recyrstallization from petroleum ether gave 58 g of 1-cyanomethyl-2,2,6,6-tetramethyl-4-piperidinyl undecanoate having a melting point of 54° C.

(b) 40 g of the product of (a) were hydrogenated as in Example 4b. Filtration and concentration gave 40 g of 1-β-aminoethyl-2,2,6,6-tetramethyl-4-piperidinyl undecanoate in the form of an oily residue which was suitable for further reaction.

(c) 20 g of the product of (b) were reacted with tetramethylolacetylenediurea as in Example 4c. Concentrating and recrystallization from acetonitrile gave 13 g of a compound of the formula

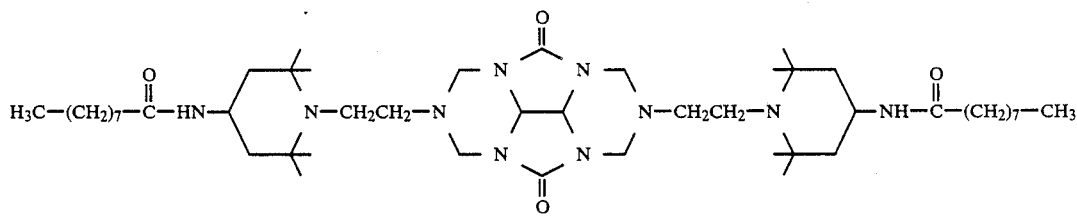

having a melting point of 142° C.

Calc.: C 67.4 H 10.2 N 12.1 O 10.4. Found: C 67.5 H 10.3 N 11.8 O 10.2.

EXAMPLE 8

(a) 66 g of 2,2,6,6-tetramethyl-4-piperidinyl benzoate were reacted as in Example 6a. Evaporation in a rotary evaporator and recrystallization from isopropanol and methanol gave 56.8 g of 1-cyanomethyl-2,2,6,6-tetramethyl-4-piperidinyl benzoate having a melting point of 147° C.

Calc.: C 72.0 H 8.0 N 9.3 O 10.7. Found: C 72.3 H 8.1 N 9.3 O 10.7.

(b) 40 g of the product of (a) were hydrogenated as in Example 4b. Filtration and concentrating left an oily residue comprising 1-β-aminoethyl-2,2,6,6-tetramethyl-4-piperidinyl benzoate, which was directly used in Example 8c.

(c) 40 g of the product of (b) were reacted with tetramethylolacetylenediurea and the product purified, both steps being carried out analogously to Example 4c, to give 27.5 g of a compound of the formula

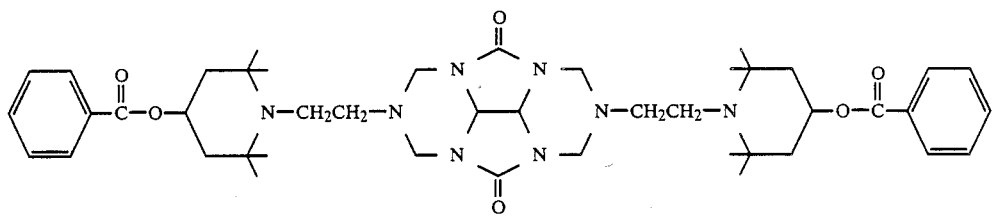

having a melting point of 211° C.

Calc.: C 66.2 H 7.8 N 14.0 O 12.0. Found: C 66.1 H 8.0 N 13.9 O 11.9.

EXAMPLE 9

(a) 45 g of 2,2,6,6-tetramethyl-4-piperidinyl 2,4-dimethylfuran-3-carboxylate were reacted analogously to Example 6a. The product was filtered with suction and recrystallized from isopropanol to give 37.9 g of 1-cyanomethyl-2,2,6,6-tetramethyl-4-piperidinyl 2,4-dimethylfuran-3-carboxylate having a melting point of 156° C.

Calc.: C 67.9 H 8.2 N 8.8 O 15.1. Found: C 67.7 H 8.4 N 8.7 O 14.9.

(b) 30 g of the product of (a) were hydrogenated in analogy to Example 4b. Filtration and concentrating gave 1-$\beta$-aminoethyl-2,2,6,6-tetramethyl-4-piperidinyl 2,4-dimethylfuran-3-carboxylate in the form of an oily residue which was usable for the reaction below without further purification.

(c) 28 g of the product of (b) were reacted with tetramethylolacetylenediurea as in Example 4c. Concentrating and recrystallization from acetonitrile gave 21.8 g of a compound of the formula

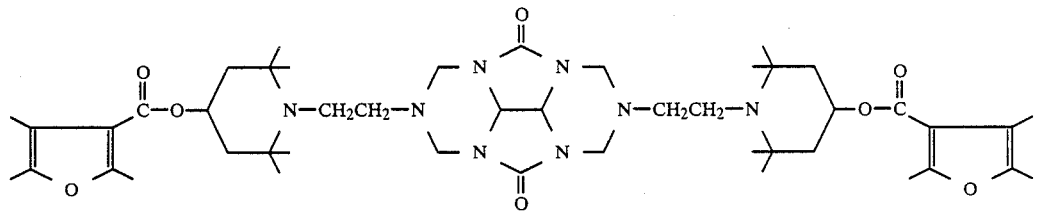

having a melting point of 206° C.

Calc.: C 63.3 H 8.0 N 13.4 O 15.3. Found: C 63.5 H 8.0 N 13.1 O 15.1.

EXAMPLE 10

(a) 107 g of 2,2,6,6-tetramethyl-4-piperidinyl 2,4,5-trimethylfuran-3-carboxylate were reacted as in Example 6a. Filtration and concentration was followed by slurrying with water, and filtering off the residue with suction and recrystallizing it twice from methanol to give 57 g of 1-cyanomethyl-2,2,6,6-tetramethyl-4-piperidinyl 2,4,5-trimethylfuran-3-carboxylate having a melting point of 88°–89° C.

Calc.: C 68.7 H 8.4 N 8.4 O 14.5. Found: C 68.7 H 8.7 N 8.1 O 14.3.

(b) 40 g of the product of (a) were hydrogenated as in Example 4b. The residue obtainable after filtration and concentration became crystalline on drying in the air. 40 g were obtained of 1-$\beta$-aminoethyl-2,2,6,6-tetramethyl-4-piperidinyl 2,4,5-trimethylfuran-3-carboxylate having a melting point of 77°–81° C.

Calc.: C 67.9 H 9.5 N 8.3 O 14.3. Found: C 67.9 H 9.6 N 7.7 O 14.6.

(c) 25 g of the product of (b) were reacted with tetramethylolacetylenediurea analogously to Example 4c. The product precipitated from the reaction mixture was filtered off with suction and washed with isobutanol, ethanol and petroleum ether to give 18.7 g of a compound of the formula

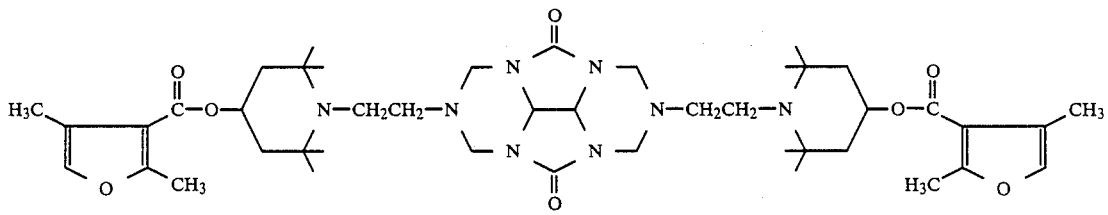

having a melting point of 228° C.

Calc.: C 64.0 H 8.1 N 13.0 O 14.8. Found: C 63.9 H 8.6 N 12.0 O 15.3.

EXAMPLE 11

(a) 48 g of bis(2,2,6,6-tetramethyl-4-piperidinyl)sebacate were reacted analogously to Example 6a. After filtration and concentrating the residue was recrystallized from isopropanol and filtered off with suction at −20° C. to give 41 g of bis(1-cyanomethyl-2,2,6,6-tetramethyl-4-piperidinyl)sebacate having a melting point of 91° C.

Calc.: C 68.8 H 9.7 N 10.0 O 11.5. Found: C 68.8 H 9.9 N 10.0 O 11.6.

(b) 34 g of the product of (a) were hydrogenated as in Example 4b. The oily residue obtained on filtration and concentrating comprises bis(1-$\beta$-aminoethyl-2,2,6,6-tetramethyl-4-piperidinyl)sebacate, and was directly usable for further reaction.

(c) 27.5 g of the product of (b) were reacted with 25.1 g of a 50% strength aqueous solution of tetramethylolacetylenediurea analogously to Example 4c. The solution was concentrated, and the residue was stirred with ice-water, filtered off with suction and washed with water. The residue was again stirred with petroleum ether, filtered off with suction, washed with petroleum ether and dried in the air to give 34 g of a compound of the formula

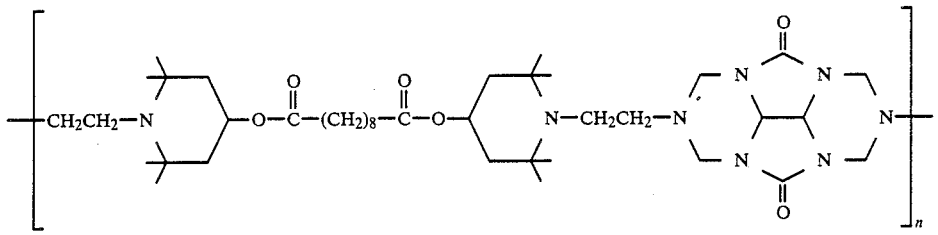

having a glass transition point of 92° C. and a decomposition point of 118°–120° C. The average molecular weight (by vapor pressure osmometry in chloroform) was 6120 g/mol.

EXAMPLE 12

20 g of the product of Example 1 were dissolved in 100 ml of pyridine. 6.2 g of adipoyl chloride were added dropwise and stirred in at room temperature for 4 h, and the mixture was then stirred at 50°–55° C. for 11 h. This was followed by stirring with petroleum ether, filtering off with suction and treating the residue with 15% strength, cold sodium hydroxide solution. The product was filtered off with suction, washed neutral with water, and dissolved in hot isobutanol. After 12 h the isobutanol was decanted off from the resulting precipitate, and the residue was stirred with petroleum ether and filtered off with suction to give 8 g of a compound of the formula

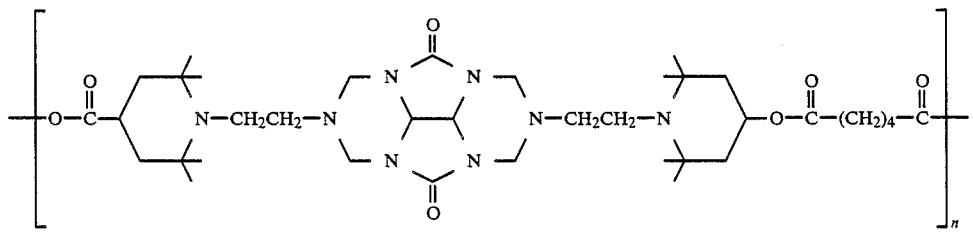

having a melting point of 206°–207° C. The average molecular weight (by vapor pressure osmometry in chloroform) was 1530 g/mol.

EXAMPLE 13

To 20 g of the product of Example 1 in 100 ml of pyridine were added 16 g of pivaloyl chloride and stirred in at room temperature for 17 h. This was followed by filtering with suction, washing with petroleum ether and stirring with 15% strength sodium hydroxide solution for 10 min. The mixture was extracted with n-butanol, and the n-butanol phase was washed with water and concentrated. Recrystallization of the residue from acetonitrile gave 14.3 g of a compound of the formula

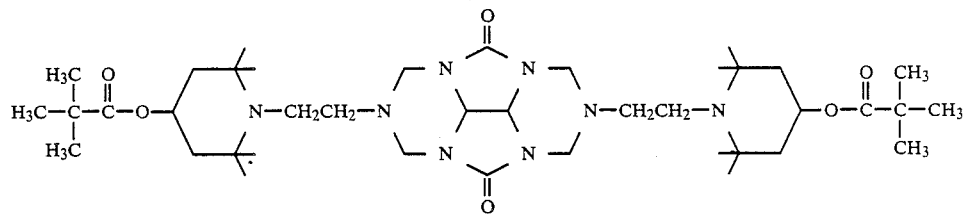

having a melting point of 210° C.

Calc.: C 64.0 H 8.3 N 14.9 O 12.8. Found: C 63.3 H 9.2 N 14.4 O 12.3.

EXAMPLE 14

(a) 205 g of N-[2,2,6,6-tetramethyl-4-piperidinyl]benzamide were reacted analogously to Example 6a. The precipitated product was filtered off with suction and recrystallized from ethanol to give 122 g of N-[1-cyanomethyl-2,2,6,6-tetramethyl-4-piperidinyl]benzamide having a melting point of 182° C.

Calc.: C 72.2 H 8.4 N 14.0 O 5.4. Found: C 72.5 H 8.5 N 13.9 O 5.4.

(b) 30 g of the product of (a) were hydrogenated analogously to Example 4c. Filtration and concentration was followed by recrystallization from toluene to give 21 g of N-[1-β-aminoethyl-2,2,6,6-tetramethyl-4-piperidinyl]benzamide having a melting point of 148° C.

Calc.: C 71.3 H 9.6 N 13.9 O 5.3. Found: C 71.3 H 9.6 N 13.6 O 5.6.

EXAMPLE 15

157.5 g of N-phenyl-N'-(2,2,6,6-tetramethyl-4-piperidinyl)urea (from 2,2,6,6-tetramethyl-4-aminopiperidine and phenyl isocyanate) were reacted analogously to Example 6a. The product was filtered off with suction and recrystallized from ethanol to give 83 g of N-phenyl-N'-(1-cyanomethyl-2,2,6,6-tetramethyl-4-piperidinyl)urea having a melting point of 218°–220° C.

Calc.: C 68.8 H 8.3 N 17.8 O 5.1. Found: C 68.8 H 8.4 N 17.8 O 5.2.

EXAMPLE 16

104 g of N-[2,2,6,6-tetramethyl-4-piperidinyl]-2,6-di-tert-butyl-4-hydroxyphenylpropionamide were reacted analogously to Example 6a. This was followed by filtering with suction, washing with ethanol, stirring up with 600 ml of dichloromethane, filtering and concentrating of the dichloromethane phase to give 59.3 g of a compound of the formula

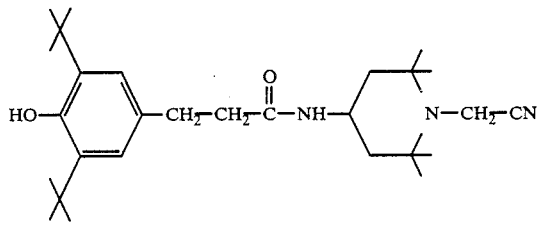

having a melting point of 213°–233° C.

Calc.: C 73.8 H 9.9 N 9.2 O 7.0. Found: C 73.5 H 10.0 N 9.0 O 6.9.

EXAMPLE 17

120 g of the reaction product of 2 mol of 2,2,6,6-tetramethyl-4-aminopiperidine and 1 mol of hexamethylenediisocyanate were reacted analogously to Example 6a. This was followed by filtering with suction, boiling with ethanol to remove ethanol-solubles, and washing with water and ethanol. Drying left 109 g of a compound of the formula

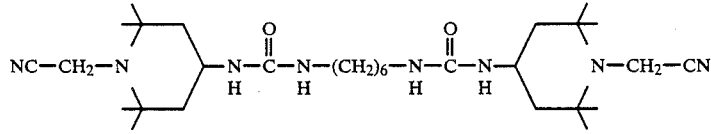

having a melting point of 223°–225° C.

EXAMPLE 18

42.2 g of N,N'-di-(2,2,6,6-tetramethyl-4-piperidinyl)urea (from urea and 2,2,6,6-tetramethyl-4-aminopiperidine) were reacted analogously to Example 6a. This was followed by filtering off with suction and recrystallizing from ethanol to give 26 g of a compound of the formula

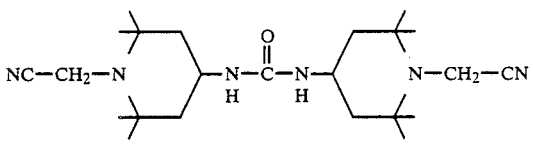

having a melting point of 264°–266° C.

EXAMPLE 19

25 g of bis(N-1,2-dimethylene-N-2,2,6,6-tetramethyl-4-piperidinyl)-2,4-dimethyl-3-furancarboxamide were reacted analogously to Example 6a. This was followed by concentrating, slurrying with ice-water, filtering off with suction at 50° C., boiling up once more with water and recrystallizing the filter residue from ethanol to give 15.1 g of a compound of the formula

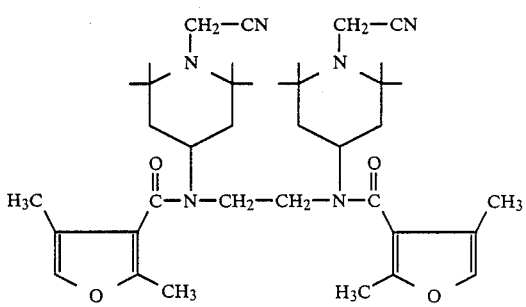

having a melting point of 265°–267° C.

Calc.: C 69.1 H 8.5 N 12.7 O 9.7. Found: C 68.4 H 8.6 N 12.4 O 10.1.

APPLICATION EXAMPLE 1

Stabilization of polyurethane

Preparation of exposure test samples of polyurethane

To a polyol component of the composition comprising 41.9 parts of a polyetherol of OH number 29.0, obtained by addition of propylene oxide and ethylene oxide onto propylene glycol and having approximately 84% primary hydroxyl groups, and 42.5 parts of a polyetherol of OH number 27.0, obtained by addition of propylene oxide and ethylene oxide on trimethylolpropane and possessing approximately 88% primary hydroxyl groups, 8.1 parts of 1,4-butanediol, 1.724 parts of a 25% strength solution of diazabicyclooctane in 1,4-butanediol, 0.016 part of dibutyltin dilaurate, 0.1 part of the silicone stabilizer OS 710 from Bayer, 5.49 parts of Frigen 11 and 0.17 part of water was added to the stabilizer mixture stated below, and the resulting mixture was foamed in a mixing ratio of 100:48.5 with a 23.0% isocyanate group containing prepolymer at 25° C. component and mold temperature into test sheets. The NCO prepolymer was prepared from 87.17 parts of 4,4'-diphenylmethane diisocyanate and 4.83 parts of a polyetherol of OH number 250, obtained by addition of propylene oxide on propylene glycol, and 8.0 parts of dipropylene glycol.

The samples were exposed in a Xenotest ®450, and the samples were assessed in terms of the yellowness index (YI) in accordance with ASTM D 1925. The results are given below

| Stabilizer mixture | Concentration (% by weight) | Yellowness index acc. to ASTM D 1925 in Xenotest 450 after | |
|---|---|---|---|
| | | 0 h | 48 h |
| Example 7c | 0.5 | | |
| Component 1 | 0.5 | 7.60 | 22.51 |
| Component 2 | 0.25 | | |
| Component 3 | 0.5 | | |
| Component 1 | 0.5 | 6.52 | 27.01 (comparison) |
| Component 2 | 0.25 | | |

Component 1 =

[structure: indole-NH-C(=O)-NH-phenyl-OC$_2$H$_5$]

Component 2 = mixture of α-tocopherol and tri(nonylphenyl) phosphite in a ratio of 1:10

Component 3 =

[structure with HN, N, N, NH groups and two C=O]

APPLICATION EXAMPLE 2

Stabilization of polypropylene (a) 0.25 part of the compound of the corresponding Example were incorporated in 100 parts of polypropylene (1320 H from BASF) by twofold extrusion at 220° C. and compression molded into 200 μm thick sheets. After 14 days' storage in the dark at 25° C. the surface of the sheets was free of any coating.

(b) The sheets produced under (a) were tested in a Xenotest ®1200 in respect of their weatherability. The aging is determined by measuring the CO number at certain time intervals. The onset of embrittlement was determined mechanically. The test results are summarized in the Table below.

| CO numbers on exposure to light in a Xenotest ® 1200 accelerated weathering tester (polypropylene) | | | |
|---|---|---|---|
| | Exposure time in (h) | | |
| Compound | 1000 | 2000 | 3000 |
| Example 1 | 4.22 | 6.89 | brittle |
| Example 2 | 4.69 | 5.55 | 7.00 |
| Example 3 | 5.25 | 5.50 | |
| Component 3 (comparison) | 5.80 | 13.09 | 21.0 |

We claim:

1. A compound of the formula I $$C-A-B-A- \quad (I)$$

-continued $$\left[-M-D-N\begin{pmatrix}R^1\end{pmatrix}\overset{\underset{\displaystyle N}{\overset{\displaystyle X}{\|}}}{\underset{\underset{\displaystyle Y}{\overset{\|}{N}}}{\underset{\displaystyle N}{\overset{\displaystyle N}{\bigcirc}}}}\begin{pmatrix}R^2\end{pmatrix}N-D-M-A-B-A\right]_n -C$$

where n is an integer from 1 to 70, $R^1$ and $R^2$ are independently of each other hydrogen, $C_1$-$C_6$-alkyl, $C_7$-$C_{12}$-phenylalkyl, methylbenzyl, phenyl, tolyl or carbo-$C_1$-$C_4$-alkoxy, or together a tetra-, penta- or hexamethylene group, or a radical of the formula

[biphenyl structure]

X and Y are independently of each other oxygen or sulfur,

M is

[structure with $R^8$, $R^3$, $R^9$, $R^4$, N—, $R^6$, $R^8$, $R^5$]

where $R^3$, $R^4$, $R^5$ and $R^6$ are identical or different and each is $C_1$-$C_4$-alkyl, or where $R^3$ and $R^4$ and also $R^5$ and $R^6$, together with the carbon atom to which they are bonded, form a 5- or 6-membered ring, and where $R^8$ is hydrogen, or together with the associated carbon atom forms a $$\diagdown\!\!\!C\!\!=\!\!O \diagup$$

group and where $R^9$ is hydrogen or a further bond to a spirolinked bridge member —B— (—A— is in this case a direct bond), the D's are identical or different and each is a (—CH$_2$—)$_n$ group, where n is from 1 to 20, or, if the radical M is bonded to —A— via the nitrogen atom, D can also be a direct bond, one or more —M—D— groups being present in the molecule where the radical —M— is bonded to —D— via its nitrogen atom, the A's are identical or different and each is oxygen, —NH—, $$-\overset{|}{N}-CO-(CH_2-)_m,$$

—NH—CO—O—  or  —NH—CO—NH—, wherein m is 0-20, or a direct bond,

B is a direct bond, $C_1$-$C_{20}$-alkylene or a bridge member of the formula
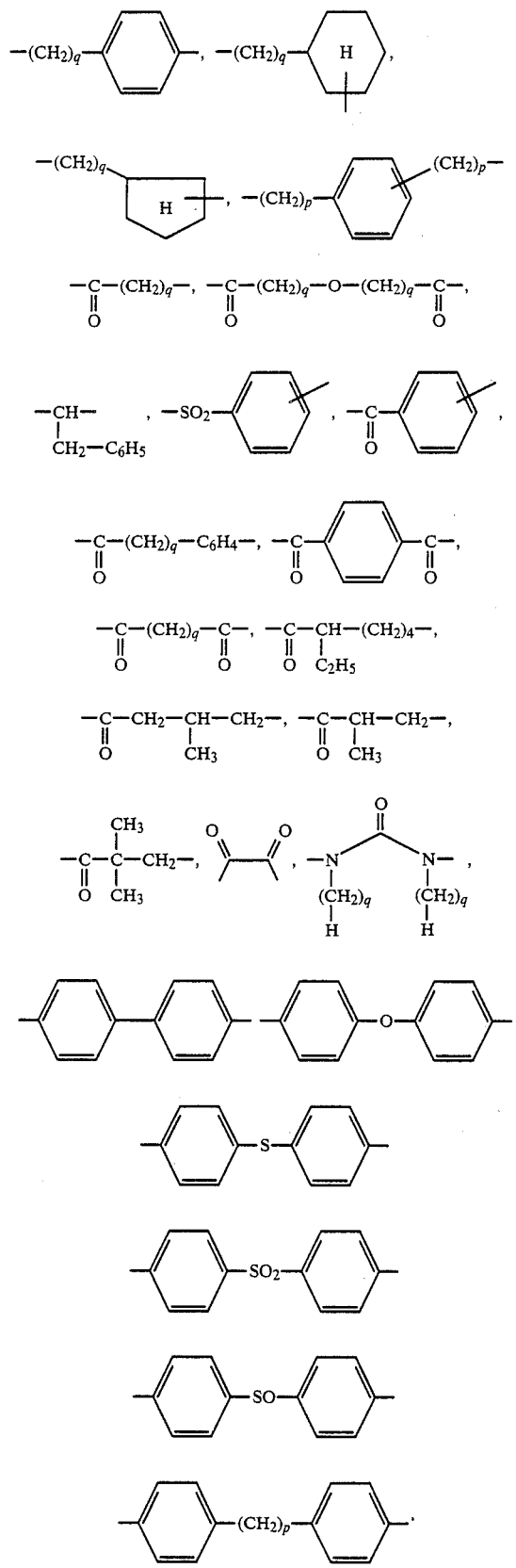
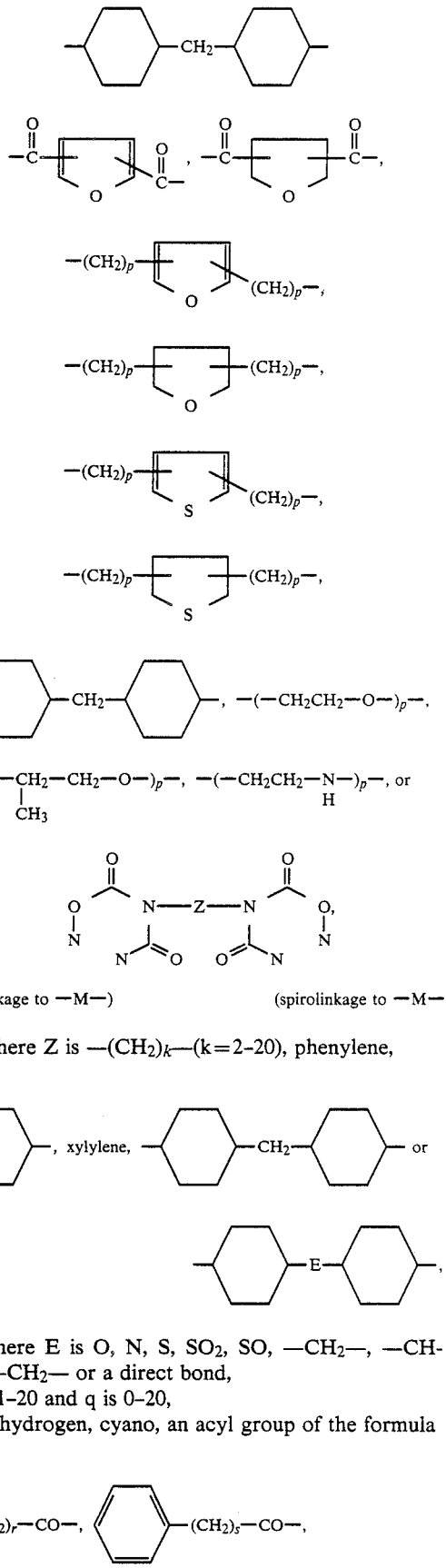
(spirolinkage to —M—)    (spirolinkage to —M—),
where Z is —$(CH_2)_k$— (k=2-20), phenylene, xylylene,
where E is O, N, S, $SO_2$, SO, —$CH_2$—, —$CH_2$—$CH_2$— or a direct bond,
p is 1-20 and q is 0-20,
C is hydrogen, cyano, an acyl group of the formula -continued

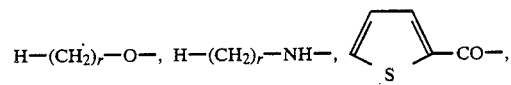

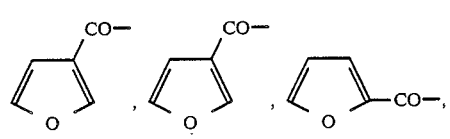

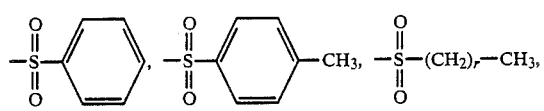

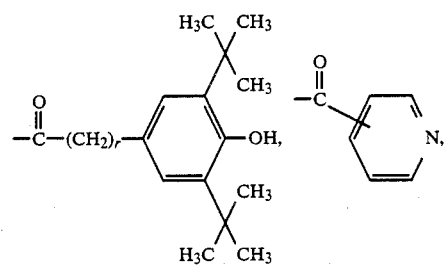

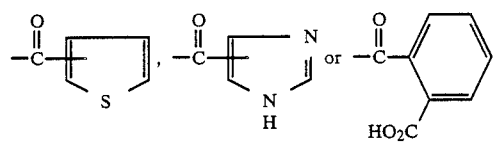

where r is 0–20 and s is 1–5,
or a heterocycle of the formula

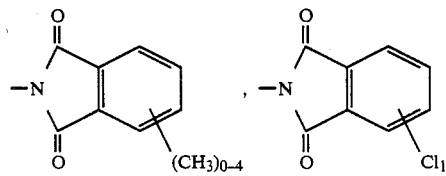

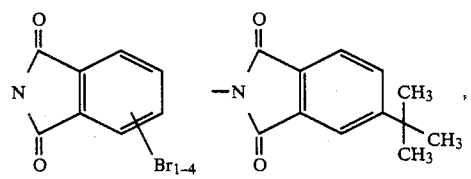

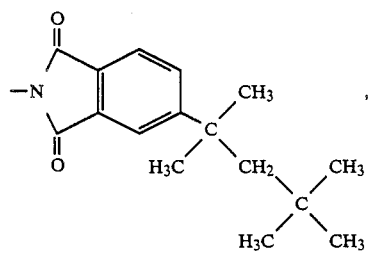

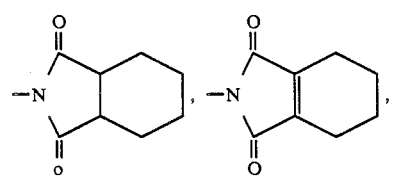

-continued

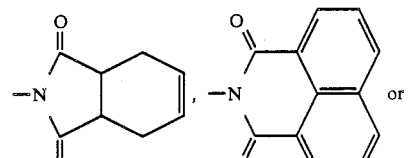

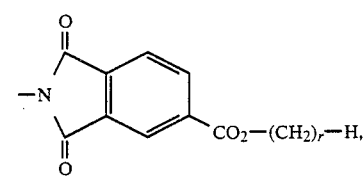

where r is 0–20 or in the formula (I) the group
—M—A—B—A—C is a group of the formula

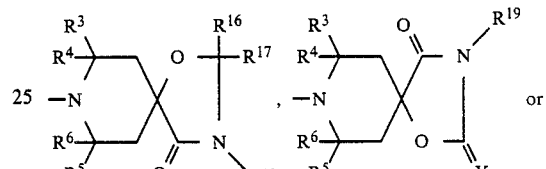

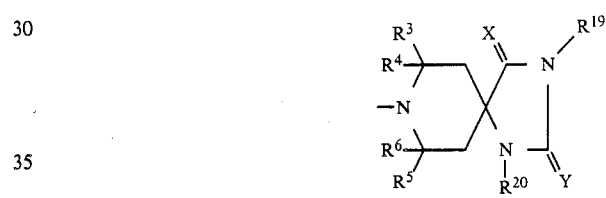

where
R$^3$ to R$^6$ and also X and Y are as defined above,
R$^{16}$ and R$^{17}$ are independently of each other hydrogen, C$_1$–C$_{22}$-alkyl, etheroxygen-, sulfur- or nitrogen-interrupted C$_1$–C$_{22}$-alkyl, or cyano-, carboxyl-, carbamoyl-, carbo-C$_1$–C$_4$-alkoxy or keto-substituted C$_1$–C$_{22}$-alkyl, C$_3$–C$_{12}$-cycloalkyl, phenyl, chlorine, C$_1$–C$_{22}$-alkyl or C$_1$–C$_{22}$-alkoxy-substituted phenyl, or C$_7$–C$_{22}$-phenylalkyl or where R$^{16}$ and R$^{17}$ together with the carbon atom joining them form a C$_5$–C$_{12}$-cycloalkyl group which may be substituted by up to 4 C$_1$–C$_4$-alkyl groups, or a group of the formula

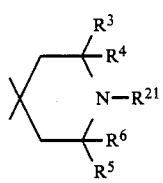

where R$^{21}$ is hydrogen, C$_1$–C$_{22}$-alkyl, which may be interrupted by etheroxygen, sulfur or nitrogen or may be substituted by cyano, hydroxyl, thiol, carboxyl, carbamoyl or carbo-C$_1$–C$_4$-alkoxy, C$_1$–C$_{22}$-alkenyl or C$_1$–C$_{22}$-alkylcarbonyl, and R$^3$, R$^4$, R$^5$ and R$^6$ have the above-mentioned meaning, R$^{18}$ is hydrogen, C$_1$–C$_{22}$-alkyl, which may be interrupted by etheroxygen, sulfur or nitrogen or may be substituted by cyano, carboxyl, carbamoyl, carbo-$C_1$-$C_4$-alkoxy, hydroxyl, thiol or amino, or $C_1$-$C_{22}$-alkylcarbonyl, $R^{19}$ is hydrogen, $C_1$-$C_{22}$-alkyl, $C_1$-$C_{22}$-alkyl which is interrupted by etheroxygen, sulfur or nitrogen or substituted by cyano or carbo-$C_1$-$C_4$-alkoxy, phenyl, phenyl substituted by chlorine, $C_1$-$C_{22}$-alkyl or $C_1$-$C_{22}$-alkoxy, $C_7$-$C_{22}$-phenylalkyl or $C_3$-$C_{12}$-cycloalkyl and $R^{20}$ is hydrogen or linear or branched $C_1$-$C_{22}$-alkyl, and the acid addition salts and hydrates thereof.

2. A compound as claimed in claim 1, wherein n is 1–20.

3. A compound as claimed in claim 1, wherein n is 1.

4. A compound as claimed in claim 2, wherein $R^1$ and $R^2$ are selected from the group consisting of hydrogen, methyl and phenyl.

5. A compound as claimed in claim 3, wherein $R^1$ and $R^2$ are selected from the group consisting of hydrogen, methyl and phenyl.

6. A compound as claimed in claim 4, wherein $R^3$, $R^4$, $R^5$ and $R^6$ are each methyl.

7. A compound as claimed in claim 5, wherein $R^3$, $R^4$, $R^5$ and $R^6$ are methyl.

8. A compound as claimed in claim 4, wherein X and Y are each oxygen.

9. A compound as claimed in claim 5, wherein X and Y are each oxygen.

10. A compound as claimed in claim 6, wherein X and Y are each oxygen.

11. A compound as claimed in claim 7, wherein X and Y are each oxygen.

12. A compound as claimed in claim 4, wherein —A— is oxygen or $$-\underset{|}{N}-\overset{OC-(CH_2)_m-H}{\vphantom{N}}$$

wherein m is 0–20.

13. A compound as claimed in claim 8, wherein —A— is oxygen or monoacylated nitrogen.

14. A compound as claimed in claim 9, wherein —A— is oxygen or $$-\underset{|}{N}-CO-(CH_2)_m-H$$

wherein m is 0–20.

15. A compound as claimed in claim 10, wherein —A— is oxygen or $$-\underset{|}{N}-CO-(CH_2)_m-H$$

wherein m is 0–20.

16. A compound as claimed in claim 11, wherein —A— is oxygen or $$-\underset{|}{N}-CO-(CH_2)_m-H$$

wherein m is 0–20.

17. A compound as claimed in claim 12, wherein —B— is a direct bond or a $C_1$-$C_{20}$-alkylene group.

18. A compound as claimed in claim 17, wherein —C— is hydrogen or $$-\underset{|}{N}-CO-(CH_2)_m-H$$

wherein m is 0–20.

* * * * *